United States Patent [19]

Schreiber et al.

[11] 4,156,944

[45] Jun. 5, 1979

[54] TOTAL ANKLE PROSTHESIS

[75] Inventors: Adam Schreiber, Küsnacht; Hans Zollinger, Zollikon; Michael Dexel, Zurich, all of Switzerland

[73] Assignee: Sulzer Brothers Limited, Winterthur, Switzerland

[21] Appl. No.: 848,647

[22] Filed: Nov. 4, 1977

[30] Foreign Application Priority Data

Nov. 15, 1976 [CH] Switzerland .................... 14341/76

[51] Int. Cl.² .............................................. A61F 1/24
[52] U.S. Cl. .................... 3/1.91; 128/92 C
[58] Field of Search ............ 3/1.91, 1.9, 1.911; 128/92 C

[56] References Cited

U.S. PATENT DOCUMENTS

| | | | |
|---|---|---|---|
| 3,872,519 | 3/1975 | Giannestras et al. | 3/1.91 |
| 3,896,502 | 7/1975 | Lennox | 3/1.91 |
| 3,987,500 | 10/1976 | Schlein | 3/1.91 |
| 4,069,518 | 1/1978 | Groth, Jr. et al. | 3/1.91 |

Primary Examiner—Ronald L. Frinks
Attorney, Agent, or Firm—Kenyon & Kenyon

[57] ABSTRACT

A total ankle prosthesis is formed of two parts, the upper part of which has a concave lower surface in saggital section while the lower part has a convex upper surface in sagittal section slidingly guided on the upper part. Each of these surfaces is of wave form in frontal cross-section with one surface having a raised central portion while the other has a guide groove receiving the raised portion. The side walls of the upper part extend downwardly past the bottom surface of the lower part to protect and avoid excess rubbing of the bottom ends of the tibia and fibula on the bottom part of the prosthesis and to discourage scar tissue between the surfaces.

3 Claims, 3 Drawing Figures

TOTAL ANKLE PROSTHESIS

This invention relates to a total ankle prosthesis.

Heretofore, total ankle prosthesis have been known in which a top part which is anchorable in the tibia and concave in sagittal section is slidably guided on a bottom part which is convex in sagittal section and anchorable in a talus. Prosthesis of these kind are known, for example, from the publication entitled "The Mayo Total Ankle Prosthesis", Form No. 1-76-11 and 11-75-20, the Depuy Company of Warsaw, Ind., U.S.A. Generally, these prosthesis have the shape of a flat hood on the top part as viewed in the frontal plane. Further, the hood generally bears on a raised cooperating member. As a result, the parts of the prosthesis, as viewed in frontal section, bear on one another substantially along a horizontal plane. Such a construction, however, often has inadequate stability against lateral buckling. Accordingly, it is an object of the invention to improve the guiding of the parts of a total ankle prosthesis on one another.

It is another object of the invention to provide a total ankle prosthesis of improved stability.

It is another object of the invention to improve the stability of an ankle prosthesis against lateral buckling.

Briefly, the invention provides a total ankle prosthesis which is comprised of an upper part for anchoring in the tibia and a lower part for anchoring in a talus. The upper part has a concave lower surface in sagittal section while the lower part has a convex upper surface in sagittal section which is slidably mounted on the concave surface of the upper part. In addition, each of the surfaces is of wave-form in frontal cross-section with one surface having a rib-like raised portion centrally thereof while the other surface has a guide groove receiving the raised portion of the other surface. Advantageously, the raised portion is formed on the upper part of the prosthesis while the guide groove is disposed on the lower part.

Since the raised portion is guided in a guide groove, the prosthesis has an increased lateral stability. Further, the prosthesis has a further advantage in that the waviness of the two parts increases the area by which the two parts bear against one another. As a result, there is a reduction in wear caused by rubbing of the two surfaces of the prosthesis on one another.

The lower part is also prvided with an anchorage surface on the bottom along with a pair of anchoring grooves in the anchorage surface. These grooves define a V therebetween in order to adapt the grooves to the shape of the talus to which the lower part of the prosthesis is anchored. The anchorage of the parts of the prosthesis can be effected in known manner, for example, by means of a bone cement.

In order to obviate excessive rubbing of the bottom ends of the tibia and fibula on the lower part of the prosthesis and on the talus, the upper part is provided with a pair of side walls which depend over the lower part. These side walls receive the lower part therebetween and extend through and beyond the bottom horizontal surface of the lower part which abuts the talus. This construction also discourages, as far as possible, the formation of scar tissue between the relatively movable surfaces.

These and other objects and advantages of the invention will become more apparent from the following detailed description and appended claims taken in conjunction with the accompanying drawings in which:

Figure 1:
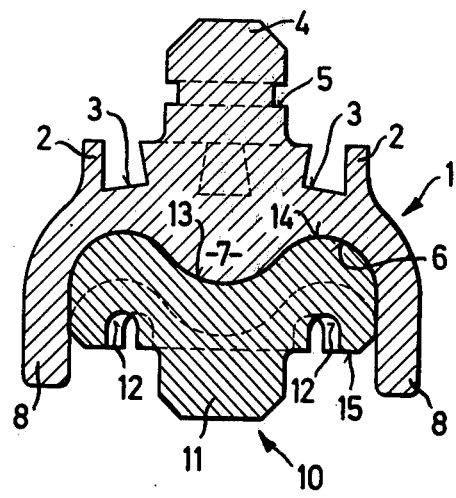
FIG. 1 illustrates a cross sectional view of a prosthesis according to the invention taken on line I—I of FIG. 2.
Figure 2:
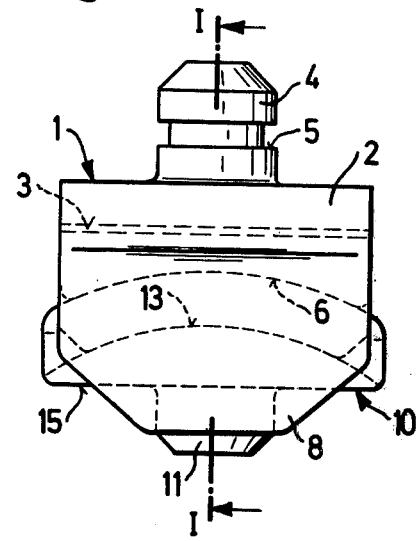
FIG. 2 illustrates a view of the prosthesis of FIG. 1 looking onto a sagittal plane.

Referring to FIGS. 1 and 2, the total ankle prosthesis is comprised of an upper part 1 which is to be anchored in a tibia (not shown) and a lower part 10 for anchoring in a talus (not shown). The upper part is provided on the top surface with a pair of elongated ribs 2, a pair of elongated grooves 3 and a cylindrical intra-medullary stem 4. The generated surface of the stem 4 is also formed with an annular recess 5. The upper part 1 is anchored via the stem 4 in the bottom end of an operatively prepared tibia (not shown). The function of the grooves 3, recess 5 and ribs 2 is to improved the adhesion of the anchoring bone cement which is usually used to anchor the upper part 1 in the tibia.

The upper part is also provided with a concave lower surface 6 as viewed in sagittal section (FIG. 2). This surface acts as an articulation, or sliding, or rubbing surface. As shown in FIG. 2, the surface 6 is cylindrical while, as shown in FIG. 1, the surface has a wave formed in frontal cross-section. In addition, the surface has a rib-like raised portion 7 which extends centrally thereof.

The lower part 10 has a convex upper surface 14 as viewed in sagittal section (see FIG. 2). This surface 14 is slidingly guided on the concave surface 6 of the upper part 1 and is also of wave form in frontal cross section. In addition, the surface 14 has a guide groove 13 for receiving the raised portion 7 of the upper part 1. In addition, the lower part 10 has an intramedullary stem 11 by which the lower part 10 can be anchored in a talus, for example, with the use of a bone cement.

Figure 3:
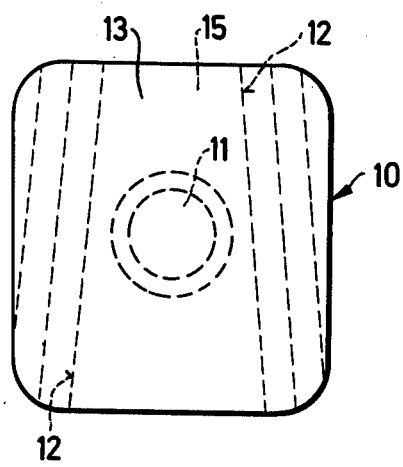
FIG. 3 illustrates an plane view of the lower part of the prosthesis of FIG. 1.

The lower part 10 also has an anchorage surface 15 on the bottom in which a pair of anchoring grooves 12 are provided. These grooves 12 are adapted to receive bone cement when the lower part 10 is anchored to the talus. Also, as shown in FIG. 3, the grooves 12 form a V to facilitate adaption to the shape of the anchorage surface of the talus.

Referring to FIG. 1, the upper part 1 also has a pair of side walls 8 which depend over the lower part 10 to receive the lower part 10 therebetween. These walls 8 extend through and beyond the horizontal bottom surface 15 of the lower part to avoid excessive rubbing between the moving parts particularly as regards movement of the downwardly extending parts on the outside of the tibia and fibula relative to the lower part 10 of the prosthesis and talus.

As indicated in FIGS. 1 and 2, the raised portion 7 of the upper part 1 is guided and mounted in the groove 13 of the lower part 10 in both the sagittal and frontal directions. As a result, there is greater surface-to-surface contact between the parts 1, 10 as well as greater lateral stability within the prosthesis.

What is claimed is:

1. A total ankle prosthesis comprising
    a lower part for anchoring in a talus, said lower part
        having a convex upper surface in sagittal section,
        and a horizontal bottom surface to abut the talus;
    an upper part for anchoring in a tibia, said upper part
        having a concave lower surface in sagittal section slidably guided on said convex surface of said lower part and a pair of side walls depending over said lower part to receive said lower part therebetween, said walls extending through and beyond said bottom surface of said lower part to obviate excessive rubbing of the bottom ends of the tibia and a fibula on said lower part and on the talus;

each of said surfaces having a wave form in frontal cross-section with one of said surfaces having a rib-like raised portion centrally thereof and the other of said surface having a guide groove receiving said raised portion.

2. A total ankle prosthesis as set forth in claim 1 wherein said raised portion is on said upper part and said guide groove is on said lower part.

3. A total ankle prosthesis as set forth in claim 1 wherein said lower part has an anchorage surface on a bottom thereof and a pair of anchoring grooves in said anchorage surface, said grooves defining a V therebetween.

* * * * *